Sept. 28, 1954 E. S. BOERNER Plant Pat. 1,306
CHRYSANTHEMUM PLANT
Filed Oct. 6, 1953
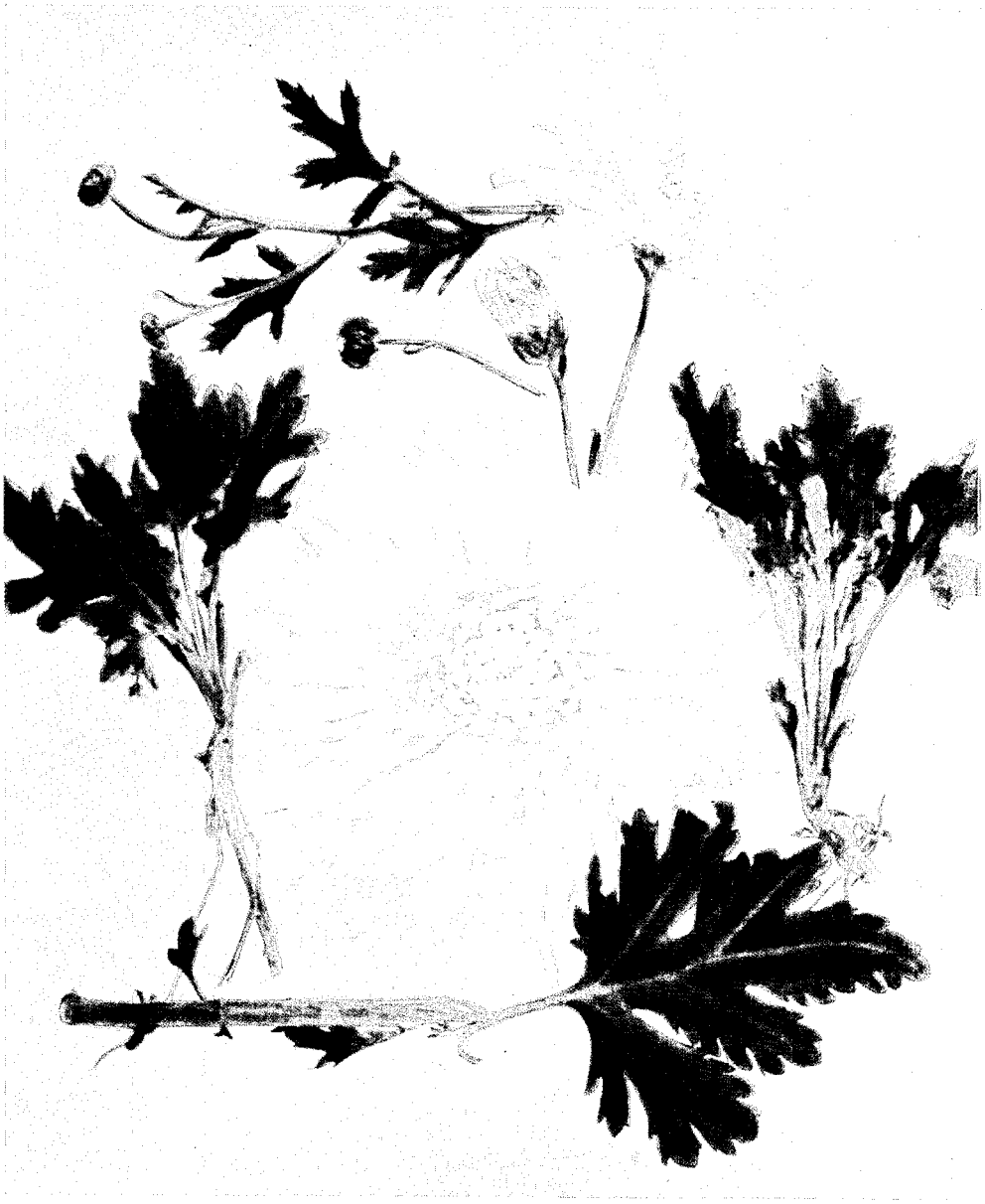
Inventor.
E. S. Boerner
By: Robb & Robb
Attorneys Patented Sept. 28, 1954

Plant Pat. 1,306

UNITED STATES PATENT OFFICE 1,306

CHRYSANTHEMUM PLANT

Eugene S. Boerner, Newark, N. Y., assignor to Jackson & Perkins Company, Newark, N. Y., a corporation of New York Application October 6, 1953, Serial No. 384,535

1 Claim. (Cl. 47—60)

The present invention relates to a new and distinct variety of chrysanthemum plant of the hardy, decorative type, which was originated by me by crossing an unnamed and unpatented seedling of the large-flowered variety known as "Nita" (unpatented) with another unnamed and unpatented $F_2$ seedling of "Chrysanthemum Rubellum Clara Curtis" (unpatented).

The primary objective of this breeding was to produce a new variety of chrysanthemum of the Chrysanthemum Rubellum type, but having flowers of larger size than are characteristic of this species. This objective was fully achieved, together with a distinctive color of the flowers of my new variety which are produced on a plant of exceptionally good vigor and winter hardiness.

The foregoing characteristics distinguish my new variety from its parents, as well as from all other varieties of the same class.

Asexual reproduction of the new variety by top cuttings and also by underground runners, at Newark, New York, shows that the foregoing characteristics and distinctions come true to form and are established and transmitted through succeeding propagations.

The accompanying drawing shows typical specimens of my new variety of chrysanthemum, with the flowers, foliage and stems in different stages of development, as depicted in color which is as nearly true as it is reasonably possible to make the same in a color illustration of this character.

The following is a detailed description of my new variety, as grown and observed in fields at Newark, New York, in the latter part of the month of September and in the late morning, with color terminology in accordance with Ridgway's Color Standards and Nomenclature:

Parentage: An unnamed seedling of "Nita" × an $F_2$ seedling of "Chrysanthemum Rubellum Clara Curtis."

Classification: Decorative.

Growth: Vigorous; upright; strong; attains a height of 3½ feet.

Cold resistance: Plants are winter hardy in northern New York; flowers burn slightly with mid-autumn frosts.

Blooming habit: In Newark, New York, climatic area, average date of beginning of bloom is about October 1st, and blooming continues until heavy freezes in October.

Bud:

*Color.*—When sepals first divide—Straw Yellow, Plate 16, lightly overcast with Alizarine Pink, Plate 13. When petals begin to unfurl—Alizarine Pink, Plate 13. When half blown—Rose Color, Plate 12; outer edges Sulphur Yellow, Plate 5.

*Peduncle.*—Color—Light Cress Green, Plate 31. Strength—strong.

Bloom:

*Size.*—5 to 5½ inches.

*Stem.*—Long; strong.

*Form.*—Decorative.

*Petalage.*—Very double and wide.

*Color.*—Center of flower—Massicot Yellow, Plate 16, lightly overcast with Spinel Pink, Plate 26. Outer petals—Thulite Pink, Plate 26, with outer edges Maize Yellow, Plate 4. Base of petals—Lumiere Green, Plate 17. Inside of petals—Deep Rose Pink, Plate 12, with outer edges Pale Yellow-Orange, Plate 3. Reverse of petals—White, Plate 53, lightly overcast with Pale Rosolane Purple, Plate 26.

*Petals.* — Texture — medium. Form — oval pointed.

Fragrance: Characteristic chrysanthemum.

Plant:

*Form.*—Upright; full; bushy.

*Growth.*—Free; many suckers.

Foliage:

*Size.*—Medium.

*Quantity.*—Normal.

*Color.*—Upper side—Dark Dull Yellow-Green, Plate 32. Reverse side—Elm Green, Plate 17.

*Texture.*—Leathery.

I claim:

A new and distinct variety of chrysanthemum plant of the hardy, decorative type, substantially as herein shown and described, characterized particularly as to novelty by the extremely large size and the distinctive color of its flowers, and by the unusual vigor and hardiness thereof as compared with other large-flowered chrysanthemums.

No references cited.